United States Patent [19]

Bissinger et al.

[11] Patent Number: 5,131,945
[45] Date of Patent: Jul. 21, 1992

[54] CERTAIN GLYOXYL-CYCLOHEXENDIONES AS HERBICIDES

[75] Inventors: Hans-Joachim Bissinger, Mainz; Ludwig Schoeder, Ingelheim; Helmut Baltruschat, Schwabenheim; Manfred Garrecht, Wackernheim; Erich Raddatz, Colombia; Wolfgang Fruhstorfer, Muehltal/Traisa, all of Fed. Rep. of Germany

[73] Assignee: Shell Research Limited, United Kingdom

[21] Appl. No.: 552,197

[22] Filed: Jul. 13, 1990

[30] Foreign Application Priority Data

Jul. 21, 1989 [DE] Fed. Rep. of Germany ....... 3924241

[51] Int. Cl.$^5$ .................... A01N 43/10; C07D 33/22
[52] U.S. Cl. ........................................ 71/90; 71/103;
71/105; 71/107; 71/108; 71/121; 71/122;
71/123; 71/113; 71/114; 71/118; 549/59;
549/61; 549/63; 549/71; 549/72; 558/412;
558/413; 558/414; 558/416; 560/64; 560/65;
560/73; 560/106; 560/118; 560/126; 562/501;
562/508; 564/306; 564/453; 564/455; 564/461;
564/426; 568/42; 568/43; 568/30; 568/31;
568/305; 568/300; 568/327; 568/328; 568/329;
568/374; 568/377

[58] Field of Search ............... 71/90, 88, 121, 122;
71/103, 123, 105, 98, 101, 108, 113, 119, 118;
568/305, 306, 327, 328, 329, 374, 377, 42, 43,
30, 31; 560/100, 64, 65, 73, 126, 118; 562/501,
508; 564/306, 453, 455, 462, 461; 549/63, 71,
72, 61, 59, 64; 558/412, 414, 413, 416

[56] References Cited

U.S. PATENT DOCUMENTS 4,202,840  5/1980  Gray et al. ..................... 71/122

FOREIGN PATENT DOCUMENTS 249151  12/1987  European Pat. Off. .......... 71/122
2215333  9/1989  United Kingdom ............... 71/122

OTHER PUBLICATIONS

R. O. Hellyer, *Aust. J. Chem.* 21, 2825 (1968).
A. C. Jain and T. R. Seshadri, *Proc. Indian Acad. Sci.* 42A, 279 (1955).

*Primary Examiner*—Richard L. Raymond
*Assistant Examiner*—Mark W. Russell

[57] ABSTRACT

Compounds of formula I

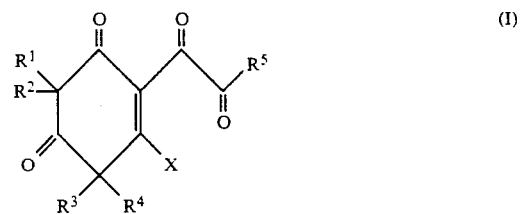

are useful as herbicides, effective against dicotyledonous weeds.

7 Claims, No Drawings

CERTAIN GLYOXYL-CYCLOHEXENDIONES AS HERBICIDES

The present invention concerns novel 2-glyoxyl-cyclohex-1-en-3,5-diones, a method for their preparation and their use as herbicides.

The compounds A (1-hydroxy-2-isobutyryl-4,4,6,6-tetramethyl-cyclohex-1-en-3,5-dione) and B (1-hydroxy-2-isovaleryl-4,4,6,6-tetramethyl-cyclohex-1-en-3,5-dione have been isolated from plants of the family Myrtaceae, plant genus Leptospermum and Xanthostemon (R.O. Hellyer, *Aust. J. Chem.* 21, 2825 (1968)) but no use is disclosed for the compounds. Also, no use is described for compound C (1-hydroxy-2-acetyl-4,4,6,6-tetramethyl-cyclohex-1-en-3,5,dione) which has been disclosed by A.C. Jain and T.R. Seshadri, in Proc. Indian Acad. Sci. 42A, 279 (1955).

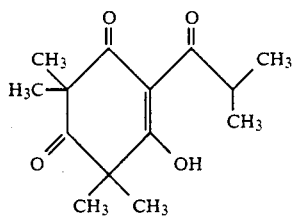

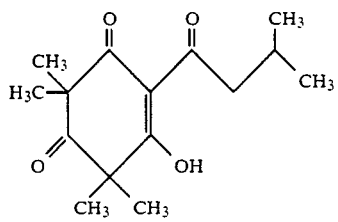

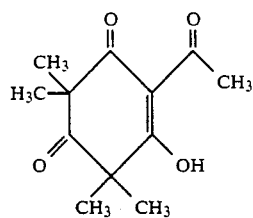

Additionally, it is known from U.S. Pat. No. 4,202,840, European Patent Specification No. 249,151A and British Patent Specification No. 2,215,333A that certain compounds of this class show herbicidal activity. However, the dosages of these herbicides required to give satisfactory herbicidal activity are quite high and, additionally, no selectivity can be observed.

We have found now that, surprisingly, certain compounds distantly related to the natural products mentioned above, show an excellent herbicidal activity at low dosages and a good selectivity of action against broad-leaf weeds.

Accordingly, the present invention provides a compound of the general formula I

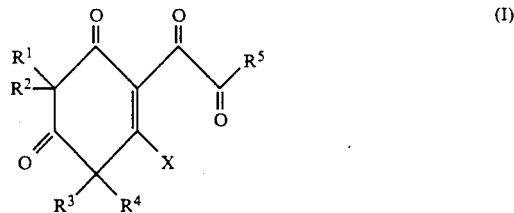

characterised in that

X represents a group OH, $OR^7$, $NH_2$, $NHR^7$, $NR^7R^8$, NOH, $NOR^7$, $OCOR^7$, $OCONHR^7$, $OCONHCOR^7$, $OCONHSO_2R^7$, $NHCONHCOR^7$, $OCOSR^7$, $NHCOSR^7$, $SCOR^7$, $SR^7$, $SCONHR^7$, $SCONHCOR^7$, $SCONHSO_2R^7$ or $SCOSR^7$;

$R^1$ to $R^4$ each independently represents a hydrogen atom or a straight-chain or branched-chain $C_{1-6}$ alkyl, $C_{2-6}$ alkenyl or $C_{2-6}$ alkynyl group which is optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups; or $R^1$ and $R^2$ and/or $R^3$ and $R^4$ together form a straight-chain or branched-chain, saturated or unsaturated, $C_{2-6}$-methylene bridge, optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups;

$R^5$ is a straight-chain or branched-chain $C_{1-20}$ alkyl, $C_{2-20}$ alkenyl or $C_{2-20}$ alkynyl group, a $C_{3-20}$ cycloalkyl, phenyl or naphthyl group, or a saturated or unsaturated heterocyclic residue having one or more heteroatoms, each of which is optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups;

$R^6$ is a straight-chain or branched-chain $C_{1-20}$ alkyl group, a $C_{3-20}$ cycloalkyl, phenyl or naphthyl group, or a saturated or unsaturated heterocyclic residue having one or more heteroatoms, each of which is optionally substituted by one or more of the same or different substituents selected from halogen atoms and CN, OH, COOH, $NO_2$, $NH_2$, $SO_3H$ and SH groups; and $R^7$ and $R^8$ each independently has the same meaning as $R^5$.

Alkyl as a substituent or as part of other substituents, such as alkoxy, may be, for example, one of the following straight-chain or branched groups depending on the number of carbon atoms indicated: methyl, ethyl, propyl, butyl, pentyl, hexyl, heptyl, octyl, nonyl, decyl, undecyl and dodecyl, including their isomers, for example, isopropyl, isobutyl, tert-butyl and isopentyl. Halogen may be fluorine, chlorine, bromine or iodine. Alkenyl, for example, may be prop-1-enyl, allyl, but-1-enyl, but-2-enyl or but-3-enyl, as well as a group having more than one double bond. Alkynyl may be, for example, prop-2-ynyl, propargyl, but-1-ynyl or but-2-ynyl. Cycloalkyl includes the following groups depending on the number of carbon atoms indicated: cyclopropyl, cyclobutyl, cyclopentyl, cyclohexyl, cycloheptyl, cyclooctyl and cyclononyl. A saturated or unsaturated heterocyclic residue is preferably derived from a saturated or unsaturated 5- or 6-membered heterocycle containing from one to four of the same or different heteroatoms, for example, nitrogen, oxygen, or sulphur. Suitable examples of such heterocycles are tetrahydrofuran, furan, tetrahydrothiophene, thiophene, pyrrolidine, pyrrole, pyrroline, pyrazole, imidazole, triazole, tetrazole, pyrazoline, oxazole, thiazole, isoxazole, isothiazole, pyran, dihydropyran, tetrahydropyran, thiopyran, dihydrothiopyran, tetrahydrothiopyran, pyridine, piperidine, pyridazine, dihydropyridazine, tetrahydropyridazine, pyrimidine, dihydropyrimidine, tetrahydropyrimidine, pyrazine, dihydropyrazine, tetrahydropyrazine, morpholine, thiazine, dihydrothiazine, tetrahydrothiazine, piperazine and triazine.

The compounds according to general formula I are oils, gums, or, predominantly, crystalline solid materials at ambient temperature ($\sim 20°$ C.). They are distinguished by their valuable biocidal properties and can be used in agriculture or related fields for the control of undesired plants, and find especial application in the selective control of broad-leaf weeds in, for example, cereal crops. Good control of undesired plants may be achieved with preferred compounds of general formula I in which X represents a group OH, $OR^7$, $OCOR^7$, $NH_2$, $NHR^7$, $NR^7R^8$, or $SR^7$;

$R^1$ to $R^4$ each independently represents a hydrogen atom or a straight-chain or branched-chain $C_{1-6}$ alkyl group optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ group, or $R^1/R^2$ and/or $R^3/R^4$ together form a straight-chain or branched-chain, saturated or unsaturated, $C_{3-5}$ methylene bridge, optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups;

$R^5$ is straight-chain or branched-chain $C_{1-8}$ alkyl, $C_{2-8}$ alkenyl or a $C_{2-8}$ alkynyl group, or a $C_{3-8}$ cycloalkyl group, each of which is optionally substituted by one or more of the same or different substituents selected from halogen atoms and CN, OH, $OR^6$, $COOR^6$, $NO_2$, $NH_2$, $NR^6_2$, $S_3H$, $SO_2R^6$ and $SR^6$ groups, or a phenyl or naphthyl group, or a saturated or unsaturated 5- or 6-membered heterocyclic residue having from one to four heteroatoms selected from nitrogen, oxygen and sulphur, each of which is optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups;

$R^6$ is a straight-chain or branched-chain $C_{1-6}$ alkyl group, a $C_{3-6}$-cycloalkyl, phenyl, or naphthyl group, or a saturated or unsaturated 5- or 6-membered heterocyclic residue having from one to four heteroatoms selected from nitrogen, oxygen and sulphur, each of which is optionally substituted by one or more of the same or different substituents selected from halogen atoms and CN, OH, COOH, $NO_2$, $NH_2$, $SO_3H$ and SH groups; and $R^7$ and $R^8$ each independently has the same meaning as $R^5$.

Preferred compounds of general formula I for control of various broad-leaf weeds are those in which X represents a group OH, $OR^7$, $OCOR^7$, $NH_2$, $NR^7R^8$, or $SR^7$;

$R^1$ to $R^4$ each independently represents a hydrogen atom or a straight-chain or branched-chain $C_{1-4}$ alkyl group optionally substituted by one or more of the same or different substituents selected from halogen atoms and OH, $OR^6$, $COOR^6$, $NH_2$ and $NR^6_2$ groups;

$R^5$, $R^7$ and $R^8$ each independently represents a straight-chain or branched-chain $C_{1-6}$ alkyl group, optionally substituted by one or more of the same or different substituents selected from halogen atoms and CN, OH, $OR^6$, $COOR^6$, $NO_2$, $NH_2$, $NR^6_2$, $SO_3H$, $SO_2R^6$ and $SR^6$ groups, or a phenyl, naphthyl or thienyl group, each of which is optionally substituted by one or more of the same or different substituents selected from halogen atoms and CN, OH, $R^6$, $OR^6$, $COOR^6$, $NO_2$, $NH_2$, $NR^6_2$, $SO_3H$, $SO_2R^6$ and $SR^6$ groups; and $R^6$ represents a straight-chain or branched-chain $C_{1-4}$ alkyl group or a phenyl group, each of which is optionally substituted by one or more of the same or different substituents selected from halogen atoms and CN, OH, COOH, $NO_2$, $NH_2$, $SO_3H$ and SH groups.

Broad-leaf weed control may be achieved both pre- and post-emergence by especially preferred compounds of general formula I in which X represents a group OH, $OR^7$, $OCOR^7$ or $NH_2$;

$R^1$ to $R^4$ each independently represents a hydrogen atom or a $C_{1-2}$ alkyl group;

$R^5$, $R^7$ and $R^8$ each independently represents a straight-chained or branched-chain $C_{1-4}$ alkyl group optionally substituted by one or more of the same or different substituents selected from halogen atoms and $OR^6$ groups, or a phenyl, naphthyl or thienyl group, each of which is optionally substituted by one or more of the same or different substituents selected from halogen atoms and $R^6$, $OR^6$ and $SO_2R^6$ groups; and $R^6$ represents a methyl or trifluoromethyl group, It will be appreciated that certain substituents will give rise to tautomeric forms of the compounds of general formula I. The present invention is to be understood to extend to all the various forms of the compounds of general formula I and mixtures thereof in whatever proportion. Thus the compounds of general formula I, their tautomers and mixtures thereof are included within the present invention, and the recitation of a compounds that exist in tautomeric form is to be understood as a recitation of their tautomers or tautomeric mixtures containing the recited compounds.

The compounds of general formula I wherein $R^1$ to $R^6$ are as defined above and X is an OH group, may be prepared by oxidising a compound of general formula II

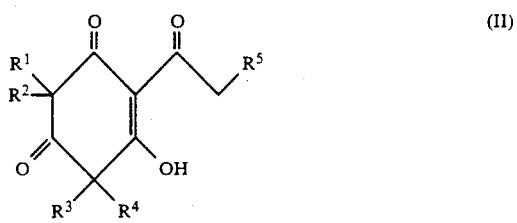

(II)

wherein $R^1$ to $R^6$ are as defined above and X is OH, which may be synthesised by the process disclosed in U.S. Pat. No. 4,202,840. These compounds may be used as isolated materials, but it is advantageous to prepare them in situ and to oxidise them subsequently in a one-pot reaction.

Preferably, the reaction is carried out as follows: Phlorphenacetophenone is used as such or alkylated with, for example, an alkyl halide, e.g. iodomethane, to yield the starting material of formula II. The subsequent oxidation may be carried out with any mild oxidising agent, such as iodine, permanganates, e.g. potassium permanganate, selenium dioxide and osmium tetroxide; however, the use of iodine or a permanganate has been found to be especially advantageous. The use of a particular solvent does not appear to be critical and both polar and aprotic solvents may be used, as well as mixtures of such solvents. However, when iodine is used for oxidation it has been found that good results may be achieved by the use of polar solvents such as lower ($C_{1-6}$, preferably $C_{1-4}$) alcohols, for example methanol and ethanol.

The reaction is performed conveniently at a temperature in the range of from 0° C. to 100° C., suitably in the range of from 5° C. to 70° C. A reaction temperature of in the range of from 10° C. to 50° C. is a suitable reaction temperature for this preparation process.

After completion of the oxidation, the resulting compounds general formula I may be isolated by any suitable conventional procedure. For example, the solvent, such as methanol, and any excess of alkyl halide used for the preparation of the intermediate of general formula II in the first reaction step may be removed by distillation, the residue then being dissolved in water, acidified and extracted with an water-immiscible organic solvent. Any excess of oxidising agent may be removed by washing the organic layer with a mild reducing agent such as aqueous sodium bisulphite. The residue obtained after evaporation of the solvent may then be further purified by crystallisation or used directly for further derivatisation, for example esterification of the 1-hydroxyl group or replacement of this group by an amine.

An alternative method of preparing compounds of general formula I in which X is an OH group is to react a compound of general formula III

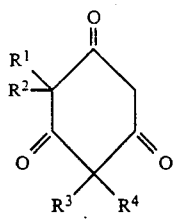
(III)

wherein $R^1$ to $R^4$ and $R^6$ are as defined above, with an acid chloride of general formula IV

ClCO—CO—$R^5$ (IV)

wherein $R^5$ and $R^6$ are as defined above.

Preferably, the reaction is carried out as follows: The cyclohexane derivative of general formula III is reacted with the acid chloride of general formula IV, preferably in the presence of an acid scavenger, especially pyridine. The reaction is performed conveniently at a temperature in the range of from 0° C. to 100° C., suitably in the range of from 5° C. to 70° C. A temperature of in the range of from 10° C. and 50° C. is a suitable reaction temperature for this method of preparation. After removal of the solvent, the residue is then dissolved in a tertiary amine and treated with a catalytic amount of acetone cyanohydrin to yield a hydroxy compound of general formula I.

After completion of the reaction the compounds of general formula I may be isolated by any suitable conventional technique. For example, the solvent may be evaporated in vacuo, the residue dissolved in water and extracted after acidification with ethyl acetate. Final purification may also be achieved by procedures such as column chromatography on silica gel.

Compounds of general formulae III and IV are either known compounds or are preparable by conventional procedures.

Compounds of general formula I in which X is other than OH may be prepared from the corresponding hydroxy compounds, directly in situ or from the isolated compounds, by methods well known to those skilled in the art, for example by esterification of the hydroxy group, or replacement of that group by an amine substituent.

The present invention also provides a herbicidal composition which comprises a compound of general formula I in association with a carrier. Preferably there are at least two carriers in a composition of the invention, at least one of which is a surface-active agent.

The present invention further provides a method of combating undesired plant growth at a locus, which may, for example, be the soil or plants in a crop area, by treating the locus with a compound or composition of the present invention. Application may be pre- or post-emergence. The dosage of active ingredient used may, for example, be in the range of from 0.01 to 10 kg of active ingredient per hectare.

Also provided by the present invention is the use of a compound of the invention as a herbicide. The compounds are particularly useful in the control of broadleaf weeds.

The compounds of general formula I may be used as such; however, they are preferably used in composition form comprising, in addition to the compounds of the invention, one or more adjuvants and auxiliaries, suitably solid and/or liquid compounds which are known for formulation purposes, and are conveniently in the form of, for example, form of, for example, emulsion concentrates, solutions which may be sprayed directly or diluted, emulsions, wettable powders, soluble powders, dusts, granulates and microcapsulates by conventional procedures. The form of application such as spraying, atomizing, dispersing and pouring and the composition form, may be selected according to the locus to be treated, the prevailing atmospheric conditions, etc.

The herbicidal compositions of the invention may be prepared by conventional procedures, e.g. intensive mixing and/or grinding of the active ingredients with other substances, such as fillers, solvents, solid carriers, and preferably surface-active compounds (tensides).

Solvents may be aromatic hydrocarbons, preferably the fractions $C_{8-12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethylene glycol mono-and di-methyl ether, ketones such as cylohexanone, strongly polar solvents such as N-methyl 2 pyrrolidone, dimethyl sulfoxide, alkyl formamides, epoxidised vegetable oils, e.g. epoxidised coconut or soybean oil, and water.

Solid carriers, which may be used for dusts or dispersible powders, may be mineral fillers, such as calcite, talc, kaolin, montmorillonite and attapulgite. The physical properties may be improved by addition of highly dispersed silica gel or highly dispersed polymers. Carriers for granulates may be porous material, e.g. pumice, broken brick, sepiolite, bentonite; non-sorptive carriers may be calcite or sand. Additionally, a multitude of pre-granulated inorganic or organic materials may be used, such as dolomite or crushed plant residues.

Suitable surface-active substances may be non-ionogenic, anionic or cationic tensides with good dispersing, emulsifying and wetting properties depending on the nature of the compound of general formula I to be formulated. Mixtures of tensides may also be used.

Suitable tensides may be so-called water-soluble soaps as well as water-soluble synthetic surface-active compounds.

Soaps usually are alkali metal, alkaline earth metal or optionally-substituted ammonium salts of higher fatty acids ($C_{10-20}$), e.g. the sodium or potassium salts of oleic or stearic acid or of mixtures of natural fatty acids which are prepared, for example, from coconut or tallow oil. Furthermore, methyl taurine salts of fatty acids may be used.

However, so-called synthetic tensides are preferably used, especially fatty sulphonates, fatty sulphates, sulphonated benzimidazole derivatives or alkyl aryl sulphonates.

The fatty sulphates or fatty sulphonates are normally used as alkali metal, alkaline earth metal or optionally substituted ammonium salts, and have an alkyl moiety of from 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with from 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Furthermore, phosphates, such as the salts of the phosphoric acid ester of a p-nonylphenol-(4-14)-ethylene oxide adduct or phospholipids, may be used.

Non-ionic tensides are preferably polyglycol ether derivatives of aliphatic or cycloaliphatic alcohols, saturated or non-saturated fatty acids and alkylphenols, which have from 3 to 10 glycol ether groups and from 8 to 20 carbon atoms in the (aliphatic) hydrocarbon residue and from 6 to 18 carbon atoms in the alkyl residue of the alkyl phenols.

Other suitable non-ionic tensides are the water-soluble, 20 to 250 ethylene glycol ether groups and 10 to 100 polypropylene glycol ether groups containing polyadducts of ethylene oxide and polypropylene glycol, ethylene diamino polypropylene glycol and alkyl polypropylene glycol with from 1 to 10 carbon atoms in the alkyl moiety; the substances suitably contain 1 to 5 ethylene glycol units per propylene glycol unit.

Examples of non-ionic tensides are nonylphenol polyethoxy ethanols, caster oil polyglycol ether, polyadducts of ethylene oxide and polypropylene, tributyl phenoxy polyethoxy ethanol, polyethylene glycol and octyl phenoxy polyethoxy ethanol.

Furthermore, fatty acid esters of polyoxyethylene sorbitan, such as polyoxyethylene sorbitan trioleate may be used.

Cationic tensides preferably are quarternary ammonium salts, which have at least one alkyl residue with from 8 to 22 carbon atoms and, furthermore, low, optionally halogenated alkyl, benzyl or hydroxyalkyl residues. The salts are preferably halides, methyl sulphates or alkyl sulphates, e.g. stearyl trimethyl ammonim chloride or benzyl bis(2-chlorethyl) ethyl ammonium bromide.

The tensides suitably used for the herbicidal compositions are described in the publications: "McCutheon's Detergents and Emulsifiers Annual", MC Publishing Corp., Ridgewood, N.J., USA 1981; H. Stache, "Tensid-Taschenbuch", 2nd ed., C. Hanser, Munich, Vienna, 1981; M. and J. Ash, "Encyclopedia of Surfactants", vol. I-III, Chemical Publishing Co., New York, N.Y., USA 1980–1981.

The herbicidal compositions of the present convention suitably comprise from 0.1% to 95%, preferably from 0.1% to 80%, by weight of at least one compound of general formula I, from 1% to 99.9% of a solid or liquid adjuvant and from 0% to 25%, preferably 0.1% to 25%, of a tenside.

Preferred composition forms and components are as follows (all percentages are by weight):

| Emulsion Concentrates: | |
| --- | --- |
| Active ingredient: | 1% to 20%, preferably 5% to 10% |
| Surface-active substance: | 5% to 30%, preferably 10% to 20% |
| Liquid carrier: | 50% to 94%, preferably 70% to 85% |
| Suspension Concentrates: | |
| Active ingredient: | 5% to 75%, preferably 10% to 50% |
| Water: | 94% to 24%, preferably 88% to 30% |
| Surface-active substance: | 1% to 40%, preferably 2% to 30% |
| Wettable Powder: | |
| Active ingredient: | 0.5% to 90%, preferably 1% to 80% |
| Surface-active substance: | 0.5% to 20%, preferably 1% to 15% |
| Solid carrier: | 5% to 95%, preferably 15% to 90% |
| Dusts: | |
| Active ingredient: | 0.1% to 10%, preferably 0.1% to 1% |
| Solid carrier: | 99.9% to 90%, preferably 99.9% to 99% |
| Granulates: | |
| Active ingredient: | 0.5% to 30%, preferably 3% to 15% |
| Solid carrier | 99.5% to 70%, preferably 97% to 85% |

Preferably the compositions are formulated in a concentrated form which is subsequently diluted by the user before application. The compositions may be diluted to a concentration of 0.001% of active ingredient (a.i.) for use. As noted above, application dosages are suitably in the range of from 0.01 to 10 kg a.i./ha.

The compositions may also comprise other auxiliaries such as, stabilizers, defoamers, viscosity controlling agents, thickeners, adhesives, fertilisers or other active ingredients, for example compounds having fungicidal or insecticidal properties, or other herbicides.

The following Example illustrate the invention.

EXAMPLE 1

1-Hydroxy-2-phenylglyoxyl-4,4,6,6-tetramethyl cyclohex-1-en-3,5-dione

Method A

Phlorphenacetophenone (27.0 g, 0.11 mol) was added to a solution of sodium (12.7 g, 0.55 mol) in methanol (400 ml). Subsequently, iodomethane (125 g, 0.88 mol) was added dropwise and the temperature maintained at 20° C.; the resulting mixture was kept at room temperature for 5 days. Then iodine (25.3 g, 0.1 mol) was added in several portions whilst the pH-value was kept between pH 7.5 and pH 8.0 by continuous addition of sodium methylate. After removal of excess methanol and iodomethane by distillation, the residue was dissolved in water. The solution was carefully acidified by addition of 2N hydrochloric acid and then extracted with diethyl ether (200 ml) three times. The collected organic layers were washed once with 10% aqueous sodium bisulphite and once with water, dried over anhydrous magnesium sulphate, and then evaporated. The residue was crystallised from isopropanol to yield a micro-crystalline material (11.4 g, 33% of theoretical) of melting point 150° C.-152° C., identified as the title compound.

Method B 4,4,6,6-Tetramethyl-1-1,3,5-cyclohexantrione (100 mg, 0.55 mmol) was dissolved in pyridine (5 ml). Phenylglyoxylic acid chloride (93 mg, 0.55 mmol) was added and the mixture was kept at 50° C. for 2 days. Then the solvent was evaporated and the residue dissolved in triethylamine (10 ml). A catalytic amount of acetone cyanohydrin (2 drops, c. 0.1 ml) was added and the reaction mixture stirred for 24 hours. Subsequently, the solvent was evaporated in vacuo, the remaining residue dissolved in water (10 ml), acidified with 2N aqueous hydrogen chloride and the solution extracted with ethyl acetate. The separated organic layer was washed with water, dried, concentrated and applied onto a column packed with silica gel, eluting with dichloromethane/acetone (9:1, v/v). 1-Hydroxy-2-phenyl-glyoxyl-4,4,6,6-tetramethyl cyclohex-1-en-3,5-dione (93 mg, 54% of theoretical; melting point: 150° C.-152° C.) was obtained.

EXAMPLE 2

1-Amino-2-phenylglyoxyl-4,4,6,6-tetramethyl cyclo-hex-1-en-3,5-dione

1-Hydroxy-2-phenylglyoxyl-4,4,6,6-tetramethyl cyclohex-1-en-3,5-dione (7.1 g, 0.23 mol), prepared as in Example 1, was dissolved in methyl tert.-butyl ether (70 ml). In an autoclave liquid ammonia (70 ml) was added to the solution and the mixture was stirred for 15 hours. Then the ammonia was evaporated off and the resulting solution was washed with a solution of concentrated hydrochloric acid (8 ml) in water (70 ml). The aqueous layer was separated and extracted twice with diethyl ether. The collected organic layers were washed twice with aqueous sodium hydroxide and once with water, dried over anhydrous magnesium sulphate and then evaporated. The colourless micro-crystalline product (4.0 g, 57% of theoretical) melted at 139° C. with decomposition and was identified as the title compound.

The identification data for the compounds of Examples 1 and 2 above, and for further compounds of general formula I prepared by analogous procedures to those described in Examples 1 to 3, are given in Table 1 below.

Further examples of compounds of general formula I encompassed by the present invention, and preparable by analogous procedures to those described in Examples 1 to 3 above, are given in Table 2 below.

TABLE 1

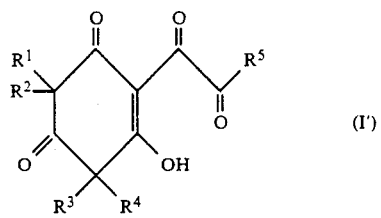

(I')

$R^1 = R^2 = R^3 = R^4 = CH_3$

| Ex. No. | $R^5$ | Melting Point (°C.) | $^1$H-NMR |
|---|---|---|---|
| 1 | –phenyl | 150–152 | 1.32(s, 6H), 1.56(s, 6H), 7.49(dd, 2H), 7.60(t, 1H), 7.89(d, 2H), 15.9(br s, 1H) |
| 3 | –C$_6$H$_4$–Me | 153–155 | 1.35(s, 6H), 1.78(s, 6H), 2.44(s, 3H), 7.33(d, 2H), 7.89(d, 2H), 15.7(br s, 1H) |
| 4 | –C$_6$H$_4$–OMe | 137–138 | 1.37(s, 6H), 1.58(s, 6H), 3.90(s, 3H), 6.99(d, 2H), 7.84(d, 2H) |

TABLE 1-continued

| | | | |
|---|---|---|---|
| 5 | 4-F-C₆H₄ | 135–136 | 1.38(s, 6H), 1.60(s, 6H), 7.21(d, 2H), 7.94(m, 2H) |
| 6 | 4-Cl-C₆H₄ | 152–155 | 1.45(s, 12H), 7.50(s, 4H) |
| 7 | 4-Br-C₆H₄ | 161–164 | 1.37(2, 6H), 1.78(s, 6H), 7.70(t, 2H), 7.74(t, 2H) |
| 8 | 2,6-Cl₂-C₆H₃ | oil | 1.38(s, 6H), 1.43(s, 6H), 7.08–7.35 (m, 3H), 13.80(s, 1H) |
| 9 | 3,4-Cl₂-C₆H₃ | 152–155 | 1.35(s, 6H), 1.60(s, 6H), 7.43(m, 3H), 8.12(d, 1H) |
| 10 | 3-Cl-C₆H₄ | 138–140 | 1.37(s, 6H), 1.59(s, 6H), 7.46(t, 1H), 7.60(d, 1H), 7.75(d, 1H), 7.83(d, 1H) |
| 11 | 2-OMe-C₆H₄ | 152–154 | 1.37(s, 6H), 1.59(s, 6H), 3.74(s, 3H), 6.98(d, 1H), 7.12(t, 1H), 7.59(t, 1H), 8.13(d, 1H), 15.75(br s, 1H) |
| 12 | 2-thienyl | 158–161 | 1.38(s, 6H), 1.58(s, 6H), 7.22(dd, 1H), 7.67(d, 1H), 7.83(d, 1H) |
| 13 | -n-Pr | oil | 0.97(t, 3H), 1.39(s, 6H), 1.45(s, 6H), 1.64(quint, 2H), 2.99(dd, 2H), 13.31(s, 1H) |
| 14 | -n-Bu | oil | 0.89(t, 3H), 1.38(m, 9H), 1.43(s, 6H), 1.64(m, 2H), 2.98(t, 2H), 13.31(s, 1H) |
| 15 | 3,4-(OMe)₂-C₆H₃ | oil | 1.31(s, 6H), 1.43(s, 6H), 3.86(s, 3H), 3.89(s, 3H), 6.82(m, 3H), 13.63(s, 1H) |

TABLE 1-continued

| Ex. No. | Compound (substituent) | Melting Point (°C.) | ¹H-NMR |
|---|---|---|---|
| 16 | 3-OCH₃-phenyl | 109–112 | 1.33(s, 6H), 1.55(s, 6H), 3.84(s, 3H), 7.15(d, 1H), 7.36(m, 2H), 7.46(m, 1H) |
| 17 | 4-OCF₃-phenyl | 133–136 | 1.32(s, 6H), 1.56(s, 6H), 7.33(d, 2H), 7.92(d, 2H) |
| 18 | 4-CF₃-phenyl | | 1.74(br.s, 12H) 7.97(m, 4H) |
| 19 | 4-SO₂CH₃-phenyl | | 1.70(br.s, 12H), 3.36(s, 3H), 8.02(d, 2H), 8.21(d, 2H) |
| 20 | 3-F,2-Cl-phenyl (2-F, 6-Cl) | 139–141 | 1.43(s, 12H), 7.22(dd, 1H), 7.41(d, 1H), 7.57(dt, 1H) |

| Ex. No. | Compound | Melting Point (°C.) | ¹H-NMR |
|---|---|---|---|
| 2 | (3,3,5,5-tetramethyl-2-amino-cyclohex-2-ene-1,4-dione with phenylglyoxalyl group) | 139 (d.) | 1.35(m, 12H), 7.20(m, 5H) |
| 21 | (3,3,5,5-tetraethyl-4-hydroxy-cyclohex-2-enone with 4-chlorophenylglyoxalyl) | oil | 0.78(2t, 6H), 0.87(t, 3H), 0.98(t, 3H), 1.87(m, 4H), 2.00(dt, 2H), 2.29(dt, 2H), 7.42(d, 2H), 7.54(d, 2H) |
| 22 | (3,3,5,5-tetramethyl-cyclohexanedione with 4-chlorophenylglyoxalyl and 3,4-dichlorobenzoyloxy) | 204–206 | |

TABLE 1-continued

| No. | Structure | m.p. (°C) | NMR |
|---|---|---|---|
| 23 | (structure) | 178–180 | |
| 24 | (structure) | 166–168 | 1.38(s, 3H), 1.42(s, 3H), 1.62(s, 3H), 1.72(s, 3H), 3.53(s, 3H), 7.39(t, 1H), 7.77(m, 3H), 7.90(2d, 2H), 8.79(d, 1H) |
| 25 | (structure) | >200 (d.) | 1.23(s, 6H), 1.54(s, 3H), 1.60(s, 3H), 2.49(s, 1H), 7.43(m, 4H), 7.53(s, 1H), 10.58(s, 1H) |
| 26 | (structure) | gum | 1.44(s, 3H), 1.45(s, 3H), 1.67(s, 3H), 1.67(s, 3H), 2.55(s, 3H), 3.40(s, 3H), 7.22(d, 1H), 7.46(m, 2H), 7.77(m, 2H), 8.61(d, 1H) |
| 27 | (structure) | 150–151 | 1.37(s, 3H), 1.43(s, 3H), 1.59(s, 3H), 1.72(s, 3H), 2.71(s, 3H), 3.54(s, 3H), 7.24(d, 1H), 7.44(d, 1H), 7.82(m, 2H), 8.03(d, 1H), 8.81(d, 1H) |

TABLE 2
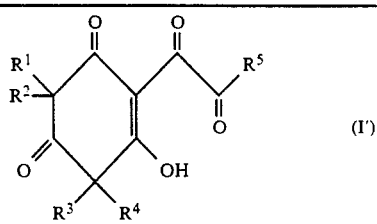
$R^1 = R^2 = R^3 = R^4 = CH_3$
| Compound No. | $R^5$ |
|---|---|
| 1. | 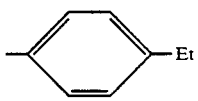 |
| 2. |  |
| 3. | 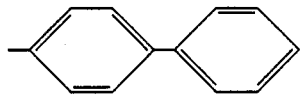 |
| 4. | 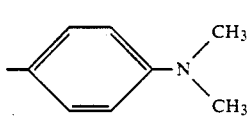 |
| 5. | 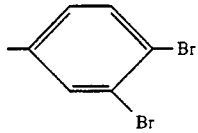 |
| 6. | 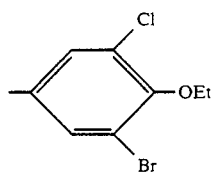 |
| 7. | 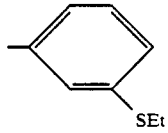 |
| 8. | 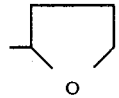 |
| 9. | 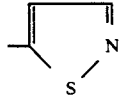 |
| 10. | 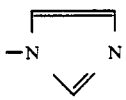 |
TABLE 2-continued
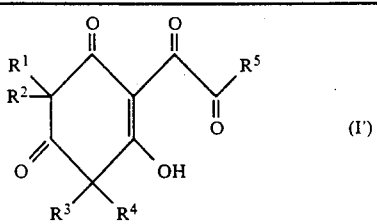
$R^1 = R^2 = R^3 = R^4 = CH_3$
| Compound No. | $R^5$ |
|---|---|
| 11. | 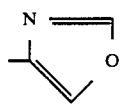 |
| 12. | 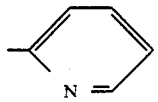 |
| 13. | 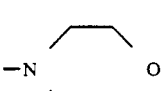 |
| 14. | 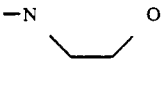 |
| 15. | 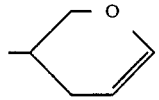 |
| 16. | 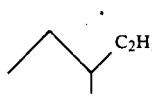 |
| 17. | 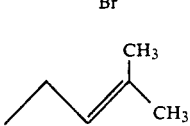 |
| 18. |  |
| 19. | 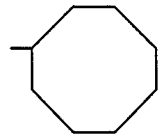 |
| 20. | 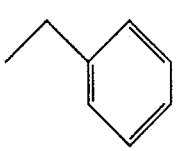 |

TABLE 2-continued $R^1 = R^2 = R^3 = R^4 = CH_3$ (I')

| Compound No. | R⁵ |
|---|---|
| 21. | 4-pyridyl |
| 22. | sec-butyl (CH(CH₃)CH₂CH₃) |
| 23. | CH₂Cl-CH(CH₃)-CH₂CH₃ (1-chloro-2-methylbutyl) |
| 24. | 3-chloro-4-(methylsulfonyl)phenyl |
| 25. | 3-methyl-4-(ethylsulfonyl)phenyl |
| 26. | 2,5-bis(trifluoromethyl)phenyl |
| 27. | 3-(trifluoromethyl)-4-(methylsulfonyl)phenyl |
| 28. | 2,4-dichloro-3,5-difluorophenyl |
| 29. | 4-morpholinopiperidin-1-yl |
| 30. | 2-methoxy-4-chloro-5-methylphenyl (OMe, Cl substituted phenyl) |
| 31. | 4-(4-chlorophenylthio)phenyl |
| 32. | C(CH₃)=N-N=N-CH₂ (methyl triazolyl) |
| 33. | C(CN)=CH-N(CH₃)₂ |
| 34. | 5-(methoxycarbonyl)naphthalen-1-yl |
| 35. | 3-methyl-7-chloro-naphthalen-1-yl |
| 36. | 3-methylnaphthalen-1-yl |
| 37. | 3-methyl-8-methylnaphthalen-2-yl |

TABLE 2-continued
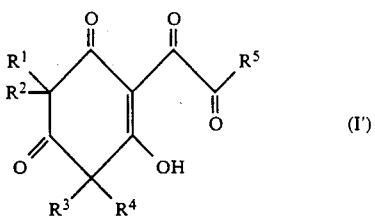
$R^1 = R^2 = R^3 = R^4 = CH_3$
| Compound No. | $R^5$ |
|---|---|
| 38. | 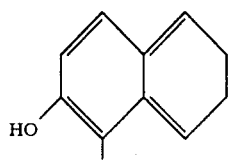 |
| 39. | 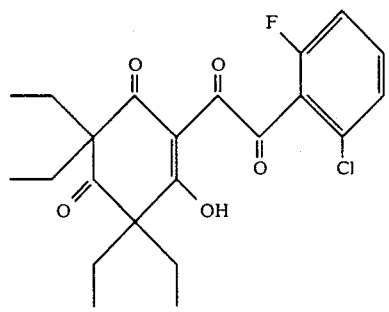 |
| 40. | 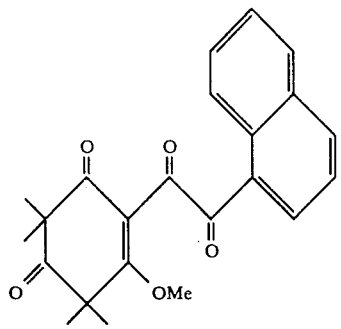 |
| 41. | 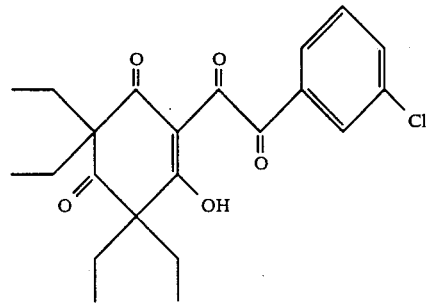 |
TABLE 2-continued
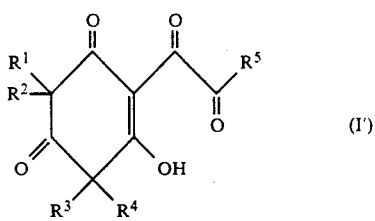
$R^1 = R^2 = R^3 = R^4 = CH_3$
| Compound No. | $R^5$ |
|---|---|
| 42. | 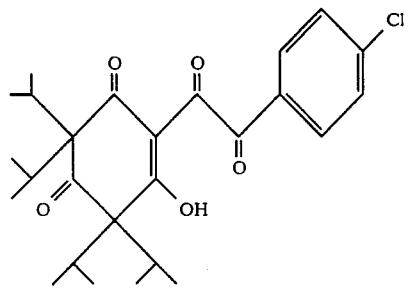 |
| 43. | 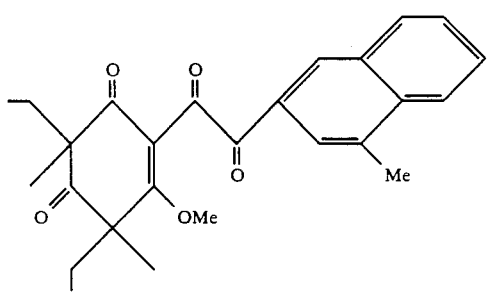 |
| 44. | 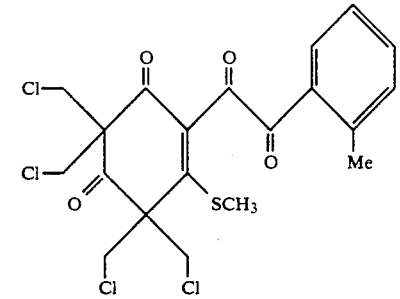 |
| 45. | 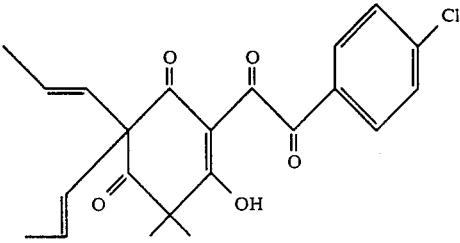 |

TABLE 2-continued

[Structure (I'): cyclohexane-dione with R1, R2, R3, R4 substituents and R5 group, with OH]

R¹ = R² = R³ = R⁴ = CH₃

| Compound No. | R⁵ |
|---|---|
| 46. | [structure with 4-Cl phenyl] |
| 47. | [spiro structure with Cl-cyclohexadiene] |
| 48. | [spiro structure with Cl-cyclohexadiene and N(ethyl)₂] |

BIOLOGICAL ACTIVITY HERBICIDAL EFFECT OF PRE-EMERGENCE TREATMENT
("pre-em")

The test plants were sown in pots at a depth of 2 cm, and on the same day the surface of the covering soil was sprayed using a spray volume of 800 l/ha and a dose rate corresponding to 2 kg/ha, using a band sprayer. The treated pots were then placed into a greenhouse. The herbicidal effect was determined after three weeks in comparison with untreated controls, using an evaluation scale of 1 to 9, where 1 represents a 100% effect and 9 no effect at all.

In this scale

| | |
|---|---|
| 1 | indicates 100% |
| 2 | indicates 100–97.5% |
| 3 | indicates 97.5–95% |
| 4 | indicates 95–90% |
| 5 | indicates 90–85% |
| 6 | indicates 85–75% |
| 7 | indicates 75–65% |
| 8 | indicates 65–32.5% |
| 9 | indicates 32.5–0% activity |

HERBICIDAL EFFECT OF POST-EMERGENCE TREATMENT
("post-em")

The test plants were sown in pots at a depth of 2 cm and precultivated to the 2.5 leaf stage (monocotyledons/grasses) or to the 1.5 metaphyll stage. The leaves were then sprayed with a band sprayer at a spray volume of 800 l/ha and a dose rate corresponding to 2 kg/ha, and the treated pots were placed into a greenhouse. The herbicidal effect was determined after three weeks in comparison to untreated controls. The evaluation method was the same as that used for the pre-emergence treatment.

The tests were carried out on the following plants:

| | |
|---|---|
| AVEFA | Avena fatua L. |
| ALOMY | Alopecurus myosuroides Huds. |
| ECHCG | Echinocloa crus-galli (L.) P. Beauv. |
| SINAL | Sinapis alba L. |
| LYPES | Lycopersicon esculentum Mill. |
| BEAVA | Beta vulgaris L. var. altissima |
| CYPES | Cyperus esculentus L. |

The results of these tests are shown in the following table, Table 3:

TABLE 3

| Compound of Example No. | PRE-EM | | | | | | | POST-EM | | | | | | |
|---|---|---|---|---|---|---|---|---|---|---|---|---|---|---|
| | AVE FA | ALO MY | ECH CG | SIN AL | LYP ES | BEA VA | CYP ES | AVE FA | ALO MY | ECH CG | SIN AL | LYP ES | BEA VA | CYP ES |
| 1 | 4 | 4 | 2 | 2 | 2 | 2 | 2 | 6 | 6 | 2 | 2 | 4 | 6 | 2 |
| 3 | 6 | 6 | 6 | 2 | 6 | 6 | 6 | 6 | 6 | 6 | 2 | 4 | 6 | 6 |
| 4 | 4 | 4 | 2 | 2 | 2 | 2 | 4 | 6 | 6 | 2 | 2 | 6 | 6 | 2 |
| 5 | 6 | 6 | 1 | 1 | 1 | 2 | 2 | 4 | 6 | 1 | 2 | 2 | 2 | 2 |
| 6 | 6 | 6 | 2 | 2 | 2 | 2 | 6 | 6 | 6 | 1 | 2 | 2 | 2 | 4 |
| 7 | 6 | 6 | 2 | 2 | 2 | 2 | 4 | 6 | 6 | 2 | 2 | 2 | 4 | 2 |
| 8 | 6 | 6 | 6 | 6 | 4 | 6 | 6 | 6 | 6 | 2 | 2 | 4 | 1 | 6 |
| 9 | 6 | 6 | 6 | 2 | 4 | 2 | 4 | 6 | 6 | 6 | 2 | 6 | 6 | 2 |
| 10 | 6 | 6 | 4 | 2 | 2 | 4 | 6 | 6 | 6 | 4 | 2 | 2 | 4 | 4 |
| 11 | 6 | 6 | 4 | 2 | 4 | 4 | 6 | 6 | 6 | 4 | 2 | 4 | 2 | 2 |
| 12 | 6 | 6 | 6 | 2 | 4 | 4 | 4 | 6 | 6 | 6 | 4 | 2 | 4 | 6 |
| 13 | | | | | | | | 6 | 6 | 4 | 2 | 1 | 1 | 4 |
| 14 | | | | | | | | 4 | 4 | 4 | 1 | 1 | 1 | 4 |
| 17 | 6 | 6 | 2 | 2 | 6 | 4 | 6 | 4 | 6 | 1 | 2 | 2 | 4 | 4 |
| 18 | 6 | 6 | 2 | 2 | 2 | 4 | 6 | 4 | 6 | 1 | 2 | 2 | 2 | 4 |

TABLE 3-continued

| Compound of Example No. | PRE-EM | | | | | | | POST-EM | | | | | | |
|---|---|---|---|---|---|---|---|---|---|---|---|---|---|---|
| | AVE FA | ALO MY | ECH CG | SIN AL | LYP ES | BEA VA | CYP ES | AVE FA | ALO MY | ECH CG | SIN AL | LYP ES | BEA VA | CYP ES |
| 19 | | | | | | | | 6 | 6 | 6 | 4 | 4 | 6 | 6 |
| 20 | 6 | 6 | 4 | 2 | 2 | 4 | 4 | 6 | 6 | 2 | 2 | 4 | 1 | 6 |
| 23 | 6 | | 6 | 4 | 4 | | | 6 | | 6 | 6 | 4 | | |
| 24 | 6 | | 4 | 2 | 4 | 4 | | 6 | | 6 | 2 | 4 | | |
| 25 | 6 | 6 | 4 | 2 | 2 | 2 | 4 | 6 | 6 | 4 | 2 | 2 | 4 | 6 |
| 26 | 6 | 6 | 6 | 6 | 4 | 6 | 6 | 6 | 6 | 6 | 4 | 4 | 6 | 6 |
| 27 | 6 | 6 | 6 | 6 | 4 | 6 | 6 | 6 | 6 | 6 | 4 | 4 | 6 | 4 |

We claim:

1. A compound of the general formula I

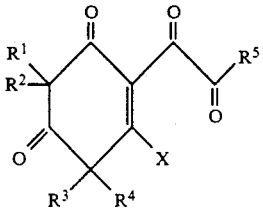

wherein

X represents a group OH, $OR^7$, $NH_2$, $NHR^7$, $NR^7R^8$, NOH, $NOR^7$, $OCOR^7$, $OCONHR^7$, OCONHCOR$^7$, $OCONHSO_2R^7$, $NHCONHCOR^7$, $OCOSR^7$, $NHCOSR^7$, $SCOR^7$, $SR^7$, $SCONHR^7$, $SCONHCOR^7$, $SCONHSO_2R^7$ or $SCOSR^7$;

$R^1$ to $R^4$ each independently represents a hydrogen atom or a straight-chain or branched-chain $C_{1-6}$ alkyl, $C_{2-6}$ alkenyl or $C_{2-6}$ alkynyl group which is optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups;

$R^1$ and $R^2$ and/or $R^3$ and $R^4$ together form a straight-chain or branched-chain, saturated or unsaturated, $C_{2-6}$-methylene bridge, optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups;

$R^5$ is a straight-chain or branched-chain $C_{1-20}$ alkyl, $C_{2-20}$ alkenyl or $C_{2-20}$ alkynyl group, a $C_{3-20}$ cycloalkyl, phenyl, naphthyl or thienyl group, each of which is optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups;

$R^6$ is a straight-chain or branched-chain $C_{1-20}$ alkyl group, a $C_{3-20}$ cycloalkyl, phenyl or naphthyl group, each of which is optionally substituted by one or more of the same or different substituents selected from halogen atoms and CN, OH, COOH, $NO_2$, $NH_2$, $SO_3H$ and SH groups; and $R^7$ and $R^8$ each independently has the same meaning as $R^5$.

2. A compound as claimed in claim 1 wherein

X represents a group OH, $OR^7$, $OCOR^7$, $NH_2$, $NHR^7$, $NR^7R^8$, or $SR^7$;

$R^1$ to $R^4$ each independently represents a hydrogen atom or a straight-chain or branched-chain $C_{1-6}$ alkyl group optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ group, or $R^1/R^2$ and/or $R^3/R^4$ together form a straight-chain or branched-chain, saturated or unsaturated, $C_{3-5}$ methylene bridge, optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups;

$R^5$ is straight-chain or branched-chain $C_{1-8}$ alkyl, $C_{2-8}$ alkenyl or a $C_{2-8}$ alkynyl group, or a $C_{3-8}$ cycloalkyl group, each of which is optionally substituted by one or more of the same or different substituents selected from halogen atoms and CN, OH, $OR^6$, $COOR^6$, $NO_2$, $NH_2$, $NR^6{}_2$, $SO_3H$, $SO_2R^6$ and $SR^6$ groups, or a phenyl, naphthyl or thienyl group, each of which is optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups;

$R^6$ is a straight-chain or branched-chain $C_{1-6}$ alkyl group, a $C_{3-6}$-cycloalkyl, phenyl, or naphthyl group, each of which is optionally substituted by one or more of the same or different substituents selected from halogen atoms and CN, OH, COOH, $NO_2$, $NH_2$, $SO_3H$ and SH groups; and $R^7$ and $R^8$ each independently has the same meaning as $R^5$.

3. A compound as claimed in claim 1 wherein

X represents a group OH, $OR^7$, $OCOR^7$, $NH_2$, $NR^7R^8$, or $SR^7$;

$R^1$ to $R^4$ each independently represents a hydrogen atom or a straight-chain or branched-chain $C_{1-4}$ alkyl group optionally substituted by one or more of the same or different substituents selected from halogen atoms and OH, $OR^6$, $COOR^6$, $NH_2$ and $NR^6{}_2$ groups;

$R^5$, $R^7$ and $R^8$ each independently represents a straight-chain or branched-chain $C_{1-6}$ alkyl group, optionally substituted by one or more of the same or different substituents selected from halogen atoms and CN, OH, $OR^6$, $COOR^6$, $NO_2$, $NH_2$, $NR^6{}_2$, $SO_3H$, $SO_2R^6$ and $SR^6$ groups, or a phenyl, naphthyl or thienyl group, each of which is optionally substituted by one or more of the same or different substituents selected from halogen atoms and CN, OH, $R^6$, $OR^6$, $COOR^6$, $NO_2$, $NH_2$, $NR^6{}_2$, $SO_3H$, $SO_2R^6$ and $SR^6$ groups; and $R^6$ represents a straight-chain or branched-chain $C_{1-4}$ alkyl group or a phenyl group, each of which is optionally substituted by one or more of the same or different substituents selected from halogen atoms and CN, OH, COOH, $NO_2$, $NH_2$, $SO_3H$ and SH groups.

4. A compound as claimed in claim 1 wherein

X represents a group OH, OR$^7$, OCOR$^7$ or NH$_2$;

R$^1$ to R$^4$ each independently represents a hydrogen atom or a C$_{1-2}$ alkyl group;

R$^5$, R$^7$ and R$^8$ each independently represents a straight-chained or branched-chain C$_{1-4}$ alkyl group optionally substituted by one or more of the same or different substituents selected from halogen atoms and OR$^6$ groups, or a phenyl, naphthyl or thienyl group, each of which is optionally substituted by one or more of the same or different substituents selected from halogen atoms and R$^6$, OR$^6$ and SO$_2$R$^6$ groups; and R$^6$ represents a methyl or trifluoromethyl group, 5. A herbicidal composition which comprises an effective amount of a compound as claimed in claim 1, in association with a carrier.

6. A method of combating undesired plant growth at a locus which comprises treating the locus with an effective amount of a compound as claimed in claim 1.

7. A method of combating undesired plant growth at a locus which comprises treating the locus with an effective amount of a composition as claimed in claim 5.

* * * * *

UNITED STATES PATENT AND TRADEMARK OFFICE
CERTIFICATE OF CORRECTION

PATENT NO. : 5,131,945

DATED : July 21, 1992

INVENTOR(S) : BISSINGER ET AL.

It is certified that error appears in the above-identified patent and that said Letters Patent is hereby corrected as shown below:

On the cover page, after "Inventors:", it should read:
--Hans-Joachim Bissinger, Mainz;

Ludwig Schroeder, Ingelheim; Helmut Baltruschat, Schwabenheim;

Manfred Garrecht, Wackernheim;

Wolfgang Fruhstorfer, Muehltal/Traisa, all of Fed. Rep. of Germany; and Erich Raddatz, Cali, Colombia--.

Signed and Sealed this

Tenth Day of August, 1993

MICHAEL K. KIRK

Attesting Officer

Acting Commissioner of Patents and Trademarks